(12) United States Patent
Zhao

(10) Patent No.: US 12,311,197 B2
(45) Date of Patent: May 27, 2025

(54) SYSTEMS AND METHODS FOR GENERATING RADIATION TREATMENT PLAN

(71) Applicant: SHANGHAI UNITED IMAGING HEALTHCARE CO., LTD., Shanghai (CN)

(72) Inventor: Kejun Zhao, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 359 days.

(21) Appl. No.: 17/805,231

(22) Filed: Jun. 2, 2022

(65) Prior Publication Data

US 2022/0387821 A1 Dec. 8, 2022

(30) Foreign Application Priority Data

Jun. 2, 2021 (CN) .......................... 202110616075.2

(51) Int. Cl.
*A61N 5/00* (2006.01)
*A61N 5/10* (2006.01)

(52) U.S. Cl.
CPC .......... *A61N 5/1031* (2013.01); *A61N 5/1036* (2013.01); *A61N 5/1047* (2013.01)

(58) Field of Classification Search
CPC ... A61N 5/1031; A61N 5/1036; A61N 5/1047
See application file for complete search history.

(56) References Cited

U.S. PATENT DOCUMENTS

| 2014/0330064 A1* | 11/2014 | Xing .................... A61N 5/1031 600/1 |
| 2018/0345042 A1* | 12/2018 | Voronenko .......... A61N 5/1081 |
| 2022/0088410 A1* | 3/2022 | Hibbard ............... A61N 5/1038 |

FOREIGN PATENT DOCUMENTS

| CN | 105617535 A | 6/2016 |
| CN | 111714790 A | 9/2020 |

* cited by examiner

*Primary Examiner* — Dani Fox
(74) *Attorney, Agent, or Firm* — METIS IP LLC

(57) ABSTRACT

The present disclosure provides a system and method for generating radiation treatment plan. The method may include obtaining a plurality of beam angles of an arc for radiation treatment and preliminary segment parameters of control points associated with the plurality of beam angles. The method may also include grouping the plurality of beam angles into at least two sets so that each pair of two consecutive beam angles of the plurality of beam angles belong to different sets of the at least two sets, and determining the target segment parameters of the control points in each of the at least two sets by optimizing, based on a leaf motion constraint, the preliminary segment parameters of the control points associating with the plurality of beam angles. The method may further include generating a treatment plan based on the target segment parameters.

20 Claims, 8 Drawing Sheets

800

Determining optimized segment parameters of the control points in each of the at least two sets by optimizing, based on the first leaf motion constraint and the second leaf motion constraint, the preliminary segment parameters of the control points in each of the at least two sets — 810

Regrouping the plurality of beam angles into multiple sets so that each pair of two consecutive beams angles of the plurality of beam angles belong to different sets of the multiple sets — 820

Determining second optimized segment parameters of control points in each of the multiple sets based on the first leaf motion constraint, the second leaf motion constraint, and the optimized segment parameters of the control points of the plurality of beam angles — 830

FIG. 8

SYSTEMS AND METHODS FOR GENERATING RADIATION TREATMENT PLAN

CROSS-REFERENCE TO RELATED APPLICATIONS

This application claims priority to Chinese Patent Application No. 202110616075.2, filed on Jun. 2, 2021, the contents of which are hereby incorporated by reference.

TECHNICAL FIELD

The present disclosure generally relates to radiation therapy, and more particularly, to systems and methods for generating a volumetric modulated arc therapy (VMAT) treatment plan for radiation therapy.

BACKGROUND

Radiation therapy is widely used in treating cancer and several other health conditions. Volumetric modulated arc therapy (VMAT) is one of major types of the radiation therapy. The VMAT uses a rotational treatment beam with continuously modulated radiation fields (formed by motions of leaves of a multi-leaf collimator (MLC)) to treat a subject. A VMAT treatment plan for the subject is generated before the VMAT treatment is performed. A radiation dose may be delivered, according to the VMAT treatment plan, to the subject. However, VMAT treatment performed according to VMAT treatment plans generated in conventional ways have poor efficacy due to the effect of constraints on the motions of the leaves of the MLC. Thus, it may be desirable to develop systems and methods for generating a VMAT treatment plan with optimized performance.

SUMMARY

According to an aspect of the present disclosure, a system is provided. The system may include at least one storage device including a set of instructions, and at least one processor configured to communicate with the at least one storage device. When executing the set of instructions, the at least one processor may be configured to direct the system to perform the following operations. The following operations may include obtaining a plurality of beam angles of an arc for radiation treatment, wherein each of the plurality of beam angles is associated with at least one control point; obtaining preliminary segment parameters of control points associated with the plurality of beam angles, wherein preliminary segment parameters of each control point include a preliminary segment shape and a preliminary segment weight; determining target segment parameters of the control points by a target parameter determination process including: grouping the plurality of beam angles into at least two sets so that each pair of two consecutive beam angles of the plurality of beam angles belong to different sets of the at least two sets; and determining the target segment parameters of the control points in each of the at least two sets by optimizing, based on a leaf motion constraint, the preliminary segment parameters of the control points associating with the plurality of beam angles, wherein target segment parameters of each control point include a target segment shape and a target segment weight; and generating a treatment plan based on the target segment parameters of the control points in each of the at least two sets.

According to another aspect of the present disclosure, a method implemented on a computing device having a processor and a computer-readable storage device is provided. The method may include obtaining a plurality of beam angles of an arc for radiation treatment, wherein each of the plurality of beam angles is associated with at least one control point; obtaining preliminary segment parameters of control points associated with the plurality of beam angles, wherein preliminary segment parameters of each control point include a preliminary segment shape and a preliminary segment weight; determining target segment parameters of the control points by a target parameter determination process including: grouping the plurality of beam angles into at least two sets so that each pair of two consecutive beam angles of the plurality of beam angles belong to different sets of the at least two sets; and determining the target segment parameters of the control points in each of the at least two sets by optimizing, based on a leaf motion constraint, the preliminary segment parameters of the control points associating with the plurality of beam angles, wherein target segment parameters of each control point include a target segment shape and a target segment weight; and generating a treatment plan based on the target segment parameters of the control points in each of the at least two sets.

According to a further aspect of the present disclosure, a non-transitory readable medium including at least one set of instructions is provided. When executed by at least one processor of a computing device, the at least one set of instructions may direct the at least one processor to perform a method. The method may include obtaining a plurality of beam angles of an arc for radiation treatment, wherein each of the plurality of beam angles is associated with at least one control point; obtaining preliminary segment parameters of control points associated with the plurality of beam angles, wherein preliminary segment parameters of each control point include a preliminary segment shape and a preliminary segment weight; determining target segment parameters of the control points by a target parameter determination process including: grouping the plurality of beam angles into at least two sets so that each pair of two consecutive beam angles of the plurality of beam angles belong to different sets of the at least two sets; and determining the target segment parameters of the control points in each of the at least two sets by optimizing, based on a leaf motion constraint, the preliminary segment parameters of the control points associating with the plurality of beam angles, wherein target segment parameters of each control point include a target segment shape and a target segment weight; and generating a treatment plan based on the target segment parameters of the control points in each of the at least two sets.

In some embodiments, the determining the target segment parameters of the control points in each of the at least two sets by optimizing, based on a leaf motion constraint, the preliminary segment parameters of the control points associating with the plurality of beam angles includes: determining the target segment parameters of the control points in each of the at least two sets by optimizing, based on a first leaf motion constraint and a second leaf motion constraint, the preliminary segment parameters of the control points associated with the plurality of beam angles, the first leaf motion constraint relating to a motion of a leaf of a collimator between a pair of consecutive beam angles among the plurality of beam angles, the second leaf motion constraint relating to a motion of a leaf of the collimator between a pair of consecutive control points of a beam angle.

In some embodiments, the second leaf motion constraint includes a target constraint, and the first leaf motion constraint is a specific multiple of the target constraint, the specific multiple being larger than or equal to 1.

In some embodiments, the determining the target segment parameters of the control points in each of the at least two sets by optimizing, based on a first leaf motion constraint and a second leaf motion constraint, the preliminary segment parameters of the control points associated with the plurality of beam angles includes: determining the target segment parameters of the control points in each of the at least two sets by simultaneously optimizing, based on the first leaf motion constraint and the second leaf motion constraint, the preliminary segment parameters of the control points in two or more of the at least two sets.

In some embodiments, the determining the target segment parameters of the control points in each of the at least two sets by optimizing, based on a first leaf motion constraint and a second leaf motion constraint, the preliminary segment parameters of the control points associated with the plurality of beam angles includes: determining the target segment parameters of the control points in each of the at least two sets by optimizing, based on the first leaf motion constraint and the second leaf motion constraint, the preliminary segment parameters of the control points in the at least two sets in sequence, such that when preliminary segment parameters of control points in one of the at least two sets are being optimized, current segment parameters of control points in other sets of the at least two sets remain unchanged.

In some embodiments, the determining the target segment parameters of the control points in each of the at least two sets by optimizing, based on a first leaf motion constraint and a second leaf motion constraint, the preliminary segment parameters of the control points associated with the plurality of beam angles includes: determining optimized segment parameters of the control points in each of the at least two sets by optimizing, based on the first leaf motion constraint and the second leaf motion constraint, the preliminary segment parameters of the control points in each of the at least two sets; and determining the target segment parameters of the control points in each of the at least two sets in one or more iterations, each of the one or more iterations including: decreasing the first leaf motion constraint by a decrement value; updating the optimized segment parameters of the control points in each of the at least two sets based on the decreased first leaf motion constraint and the second leaf motion constraint; determining whether a termination condition is satisfied; and in response to determining that the termination condition is satisfied, designating updated segment parameters of the control points in each of the at least two sets as the target segment parameters of the control points in each of the at least two sets.

In some embodiments, the one or more iterations further include in response to determining that the termination condition is not satisfied, proceeding to a next iteration of the one or more iterations.

In some embodiments, the one or more iterations further include regrouping the plurality of beam angles into multiple sets such that each pair of two consecutive beams angles of the plurality of beam angles belong to different sets of the multiple sets; and determining second optimized segment parameters of the control points in each of the multiple sets based on the decreased first leaf motion constraint, the second leaf motion constraint, and the updated segment parameters of the control points of the plurality of beam angles.

In some embodiments, the determining the target segment parameters of the control points in each of the at least two sets by optimizing, based on a first leaf motion constraint and a second leaf motion constraint, the preliminary segment parameters of the control points associated with the plurality of beam angles includes: determining optimized segment parameters of the control points in each of the at least two sets by optimizing, based on the first leaf motion constraint and the second leaf motion constraint, the preliminary segment parameters of the control points in each of the at least two sets; and decreasing the first leaf motion constraint by a decrement value; determining whether a termination condition is satisfied; and in response to determining that the termination condition is satisfied, designating the optimized segment parameters of the control points in each of the at least two sets as the target segment parameters of the control points in each of the at least two sets.

In some embodiments, in response to determining that the termination condition is not satisfied, updating the optimized segment parameters of the control points in each of the at least two sets based on the decreased first leaf motion constraint and the second leaf motion constraint; and initiating one or more iterations, each of the one or more iterations including: further decreasing the decreased first leaf motion constraint by the decrement value; determining whether the termination condition is satisfied; and in response to determining that the termination condition is satisfied, designating the updated segment parameters of the control points in each of the at least two sets as the target segment parameters of the control points in each of the at least two sets; and in response to determining that the termination condition is not satisfied, further updating the updated segment parameters of the control points in each of the at least two sets based on the further decreased first leaf motion constraint and the second leaf motion constraint; and proceeding to a next iteration.

In some embodiments, the second leaf motion constraint includes a target constraint, the method further including: determining whether the decreased first leaf motion constraint is smaller than the target constraint; and in response to determining that the decreased first leaf motion constraint is smaller than the target constraint, adjusting the decreased first leaf motion constraint to the target constraint; and determining third optimized segment parameters of control points in each of the at least two sets based on the adjusted first leaf motion constraint and the second leaf motion constraint; and designating the third optimized segment parameters of the control points in each of the at least two sets as the target segment parameters of the control points in each of the at least two sets.

In some embodiments, the method further includes determining optimized segment parameters of the control points in each of the at least two sets by optimizing, based on the first leaf motion constraint and the second leaf motion constraint, the preliminary segment parameters of the control points in each of the at least two sets; regrouping the plurality of beam angles into multiple sets such that each pair of two consecutive beams angles of the plurality of beam angles belong to different sets of the multiple sets; and determining second optimized segment parameters of the control points in each of the multiple sets based on the first leaf motion constraint, the second leaf motion constraint, and the optimized segment parameters of the control points of the plurality of beam angles.

In some embodiments, the preliminary segment parameters of the control points of the plurality of beam angles are determined based on a second leaf motion constraint.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 8 includes a flowchart illustrating an exemplary process for optimizing the preliminary segment parameters of the control points of the plurality of beam angles according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
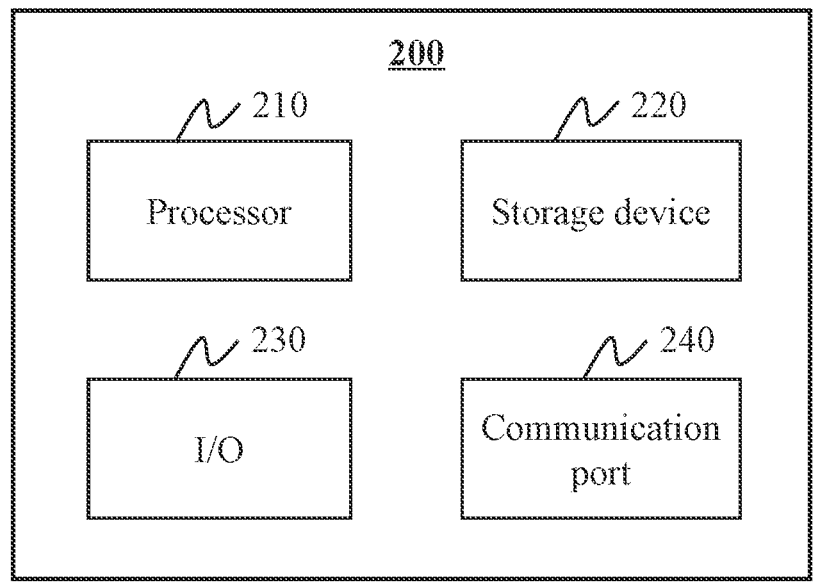
FIG. 2 is a schematic diagram illustrating an exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on a computing device (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing apparatus, for execution by the computing apparatus. Software instructions may be embedded in firmware, such as an erasable programmable read-only memory (EPROM). It will be further appreciated that hardware modules/units/blocks may be included of connected logic components, such as gates and flip-flops, and/or can be included of programmable units, such as programmable gate arrays or processors. The modules/units/blocks or computing apparatus functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "anatomical structure" in the present disclosure may refer to gas (e.g., air), liquid (e.g., water), solid (e.g., stone), cell, tissue, organ of a subject, or any combination thereof, which may be displayed in an image (e.g., a second image, or a first image, etc.) and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

Provided herein are systems and components for non-invasive imaging and/or treatment, such as for disease diagnosis, treatment or research purposes. In some embodiments, the systems may include a radiotherapy (RT) system, a computed tomography (CT) system, a positron emission tomography (PET) system, a magnetic resonance imaging (MRI) system an emission computed tomography (ECT) system, an X-ray photography system, or the like, or any combination thereof. For illustration purposes, the disclosure describes systems and methods for radiotherapy. For persons having ordinary skills in the art, a certain number of variations, changes, and/or modifications may be deduced under the guidance of the present disclosure. Those variations, changes, and/or modifications do not depart from the scope of the present disclosure.

An aspect of the present disclosure relates to an RT system. The RT system may obtain a plurality of beam angles of an arc for radiation treatment, each of the plurality of beam angles including at least one control point. The RT system may also obtain preliminary segment parameters of control points of the plurality of beam angles. The preliminary segment parameters of each control point may include a preliminary segment shape and a preliminary segment weight. The RT system may optimize the preliminary segment parameters of each control point in an optimization process. During the optimization process, the plurality of beam angles may be grouped into at least two sets such that each pair of two consecutive beam angles of the plurality of beam angles belong to different sets of the at least two sets. Target segment parameters of the control points in each of the at least two sets may be determined by optimizing, based on a first leaf motion constraint, the preliminary segment parameters of the control points of the plurality of beam angles. The target segment parameters of each control point may include a target segment shape and a target segment weight. The first leaf motion constraint may relate to a motion of a leaf of the collimator between a pair of consecutive beam angles among the plurality of beam angles. The target segment parameters of the control points in each of the at least two sets may be used to generate a treatment plan, e.g., a volumetric modulated arc therapy (VMAT) treatment plan. Radiation doses may be delivered, according to the VMAT treatment plan, to a subject.

The entire optimization process may be separated into multiple fractions. In each of the multiple fractions, preliminary segment parameters of control points in one or more sets of the at least two sets may be optimized each time. In this way, a count (or number) of variables may be reduced in each fraction and a convergency of the optimization may be reached more easily. More attention may be paid to fractions having poor optimization effect, instead of all the multiple fractions at the same time, and the efficiency of the optimization may also be improved. In the meanwhile, the target segment parameters of the control points may be determined on the condition that an execution time of the VMAT treatment is relatively short. Thus, a VMAT treatment performed according to the generated VMAT treatment plan may achieve a satisfactory efficacy within a short execution time.

Figure 1:
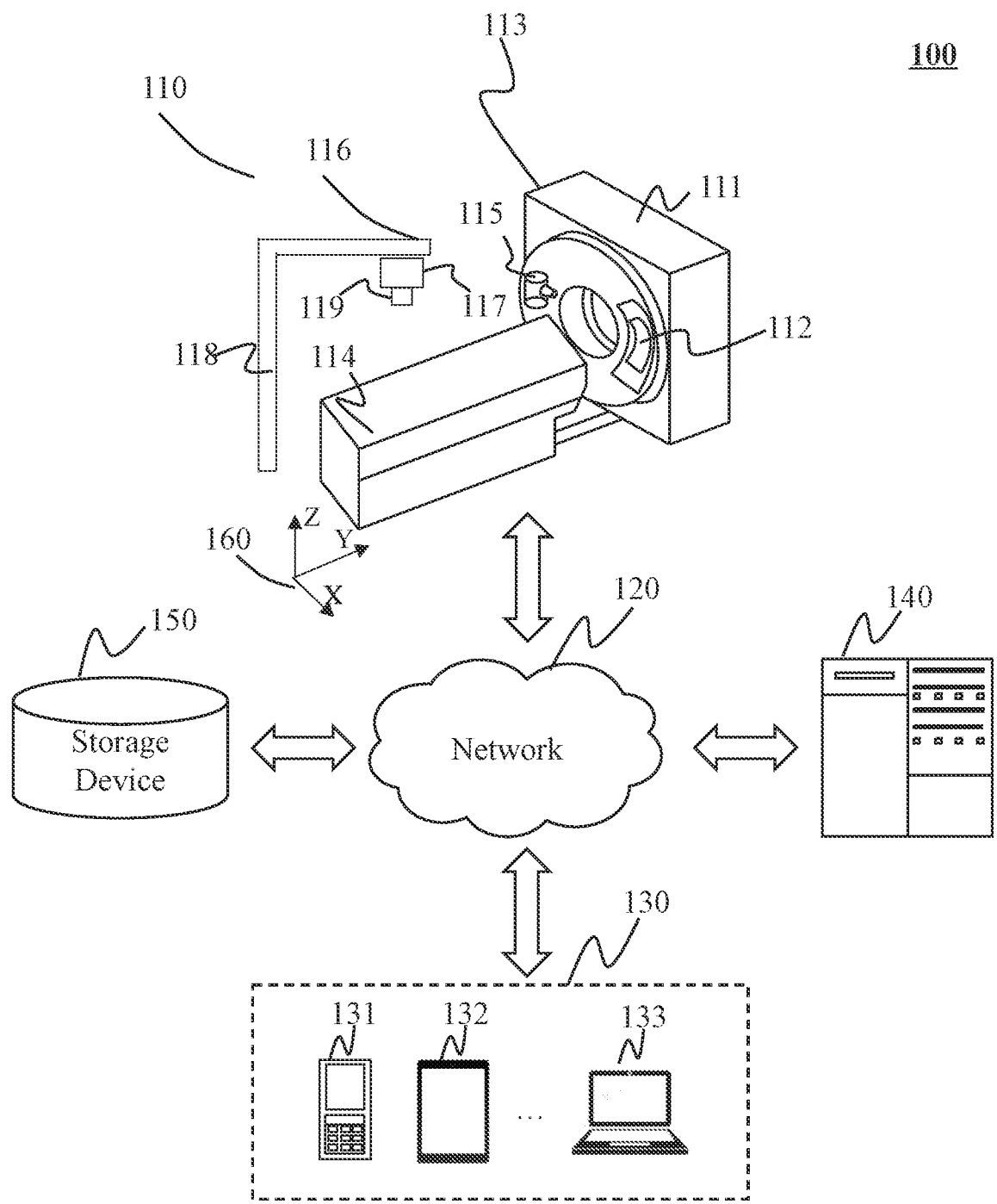
FIG. 1 is a schematic diagram illustrating an exemplary radiotherapy (RT) system according to some embodiments of the present disclosure.

FIG. 1 is a schematic diagram illustrating an exemplary RT system 100 according to some embodiments of the present disclosure. The RT system 100 may include an RT device 110, a network 120, one or more terminals 130, a processing device 140, and a storage device 150. In some embodiments, two or more components of the RT system 100 may be connected to and/or communicate with each other via a wireless connection (e.g., the network 120), a wired connection, or a combination thereof. The connection between the components of the RT system 100 may be variable. Merely by way of example, the RT device 110 may be connected to the processing device 140 through the network 120 or directly. As a further example, the storage device 150 may be connected to the processing device 140 through the network 120 or directly.

The RT device 110 may be configured to deliver a radiotherapy dose to a subject. For example, the treatment device may deliver one or more radiation beams to a treatment region (e.g., a tumor) of a subject for causing an alleviation of the subject's symptom. A radiation beam may include a plurality of radiation beamlets. In the present disclosure, "subject" and "object" are used interchangeably. The subject may include any biological subject (e.g., a human being, an animal, a plant, or a portion thereof) and/or a non-biological subject (e.g., a phantom). For example, the subject may include a specific portion of a body, such as the head, the thorax, the abdomen, or the like, or a combination thereof, of the subject. In some embodiments, the treatment device may be an image-guided radiation therapy (IGRT) device, a conformal radiation therapy device, an intensity-modulated radiation therapy (IMRT) device, an intensity-modulated arc therapy (IMAT) device, an emission guided radiation therapy (EGRT), or the like.

In some embodiments, the RT device 110 may be an IGRT device configured to acquire image data relating to the subject, and perform a radiotherapy treatment on the subject. For example, as illustrated in FIG. 1, the RT device 110 may include an imaging component 113, a treatment component 116, a table (or referred to as couch) 114, or the like. The imaging component 113 may be configured to acquire an image of the subject before radiotherapy treatment, during the radiotherapy treatment, and/or after the radiotherapy treatment. In some embodiments, the imaging component 113 may include a computed tomography (CT) device (e.g., a cone beam CT (CBCT) device, a fan beam CT (FBCT) device, a multi-slice CT (MSCT) device, etc.), a magnetic resonance imaging (MRI) device, an ultrasound imaging device, a fluoroscopy imaging device, a single-photon emission computed tomography (SPECT) device, a positron emission tomography (PET) device, an X-ray imaging device, or the like, or any combination thereof.

In some embodiments, the imaging component 113 may include an imaging radiation source 115, a detector 112, a gantry 111, or the like. The imaging radiation source 115 and the detector 112 may be mounted on the gantry 111. The imaging radiation source 115 may emit radioactive rays to the subject. The detector 112 may detect radiation events (e.g., x-ray photons, gamma-ray photons) emitted from the imaging region of the imaging component 113. In some embodiments, the detector 112 may include one or more detector units. The detector unit(s) may include a scintillation detector (e.g., a cesium iodide detector, a gadolinium oxysulfide detector), a gas detector, etc. The detector unit(s) may include a single-row detector and/or a multi-rows detector.

The treatment component 116 may be configured to deliver radiation doses to the subject. The treatment component 116 may include a treatment radiation source 117, a gantry 118, and a collimator assembly 119. The treatment radiation source 117 may be configured to emit treatment radiations towards the subject. In some embodiments, the treatment radiation source 117 may include a linear accelerator (LINAC). The collimator assembly 119 may be configured to shape a treatment beam generated by the treatment radiation source 117.

In some embodiments, the imaging component 113 may be spaced by a distance from the treatment component 116. In some embodiments, rotation axes of the gantry 111 of the imaging component 113 and the gantry 118 of the treatment component 116 may be the same or different. The subject may be positioned in different positions on the table 114 for imaging and treatment. In some embodiments, the imaging radiation source 115 and the treatment radiation source 117 may be integrated as one radiation source to image and/or treat the subject. In some embodiments, the imaging component 113 and the treatment component 116 may share the same gantry. For example, the treatment radiation source 117 may be mounted on the gantry 111 of the imaging component 113. A subject may be placed on the table 114 for treatment and/or imaging.

The couch 114 may be configured to support the subject to be treated and/or imaged. In some embodiments, the couch 114 may be movable between the treatment component 116 and the imaging component 113 along a Y-axis direction of a coordinate system 160 as shown in FIG. 1. In some embodiments, the couch 114 may be configured to rotate and/or translate along different directions to move the subject to a desired position (e.g., an imaging position under the imaging component 113 for imaging, a treatment position under the treatment component 116 for treatment, etc.).

The network 120 may include any suitable network that can facilitate the exchange of information and/or data for the RT system 100. In some embodiments, one or more components (e.g., the RT device 110, the terminal(s) 130, the processing device 140, the storage device 150, etc.) of the RT system 100 may communicate information and/or data with one or more other components of the RT system 100 via the network 120. For example, the processing device 140 may obtain image data from the RT device 110 via the network 120. As another example, the processing device 140 may obtain user (e.g., a doctor, a radiologist) instructions from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the RT system 100 may be connected to the network 120 to exchange data and/or information.

Figure 3:
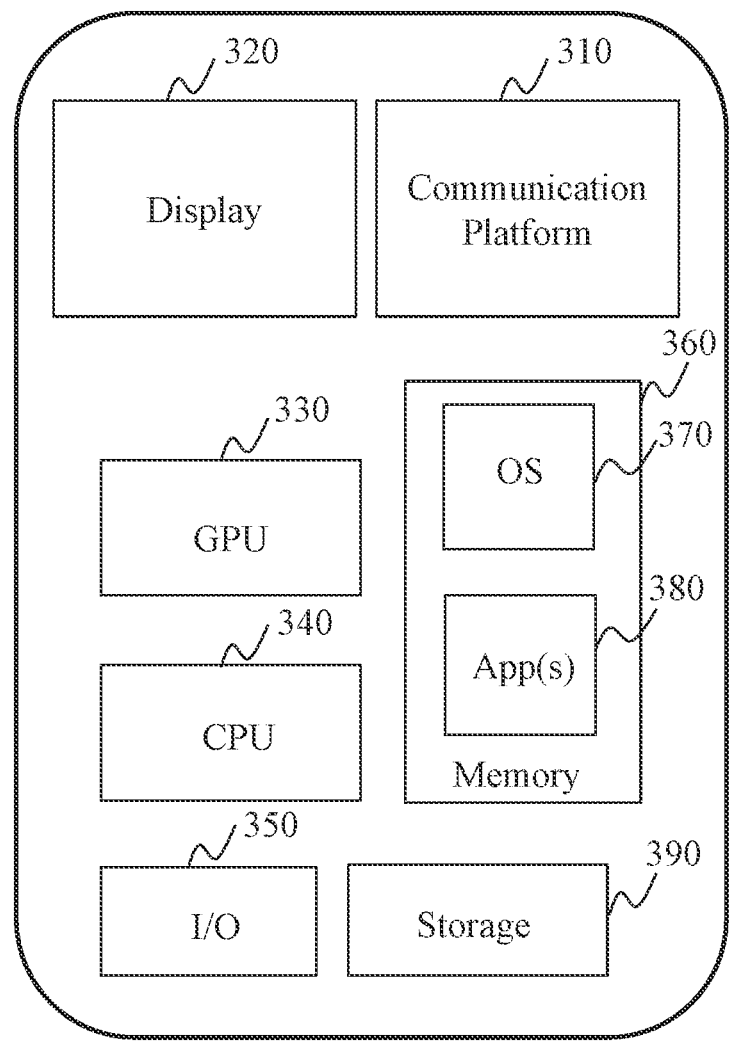
FIG. 3 is a schematic diagram illustrating hardware and/or software components of an exemplary mobile device according to some embodiments of the present disclosure.

The terminal(s) 130 may enable user interaction between a user and the RT system 100. In some embodiments, the terminal(s) 130 may be connected to and/or communicate with the RT device 110, the processing device 140, and/or the storage device 150. For example, the terminal(s) 130 may display a treatment image of the subject obtained from the processing device 140. In some embodiments, the terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Merely by way of example, the terminal(s) 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process information obtained from the RT device 110, the terminal(s) 130, and/or the storage device 150. In some embodiments, the processing device 140 may be a single server or a server group. The server group may be centralized or distributed. In some embodiments, the processing device 140 may be local or remote. For example, the processing device 140 may access information stored in the RT device 110, the terminal(s) 130, and/or the storage device 150 via the network 120. As another example, the processing device 140 may be directly connected to the RT device 110, the terminal(s) 130 and/or the storage device 150 to access stored information. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the RT device 110, the terminal(s) 130, and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components (e.g., the RT device 110, the processing device 140, the terminal(s) 130) of the RT system 100. One or more components of the RT system 100 may access the data and/or instructions stored in the storage device 150 via the network 120. In some embodiments, the storage device 150 may be directly connected to or communicate with one or more other components (e.g., the RT device 110, the processing device 140, the terminal(s) 130) of the RT system 100. In some embodiments, the storage device 150 may be part of the processing device 140.

For illustration purposes, a coordinate system 160 is provided in FIG. 1. The coordinate system 160 may be a Cartesian system including an X-axis, the Y-axis, and a Z-axis. The X-axis and the Y-axis shown in FIG. 1 may be horizontal, and the Z-axis may be vertical. As illustrated, the positive X direction along the X-axis may be from the left side to the right side of the table 114 viewed from the direction facing the front of the RT device 110; the positive Y direction along the Y-axis shown in FIG. 1 may be from the end to the head of the table 114; the positive Z direction along the Z-axis shown in FIG. 1 may be from the lower part to the upper part of the RT device 110.

It should be noted that the above description regarding the RT system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the RT system 100 may include one or more additional components and/or one or more components of the RT system 100 described above may be omitted. In some embodiments, a component of the RT system 100 may be implemented on two or more sub-components. Two or more components of the RT system 100 may be integrated into a single component. For example, the treatment component 116 in the RT device 110 may be integrated into the imaging component 113.

In some embodiments, radiation dosimetry methods disclosed herein may be implemented on a single-modality RT system, which may include an RT device (e.g., a same or similar device as the treatment component 116), the network 120, the storage device 150, the processing device 140, the terminal(s) 130, or the like, or any combination thereof. For illustration purposes, the implementation of the radiation dosimetry methods on the RT system 100 is described hereinafter, and this is not intended to be limiting.

FIG. 2 is a schematic diagram illustrating exemplary hardware and/or software components of a computing device 200 according to some embodiments of the present disclosure. The computing device 200 may be used to implement any component of the RT system 100 as described herein. For example, the processing device 140 and/or the terminal(s) 130 may be implemented on the computing device 200, respectively, via its hardware, software program, firmware, or a combination thereof. Although only one such computing device is shown, for convenience, the computer functions relating to the RT system 100 as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program code) and perform functions of the processing device 140 in accordance with techniques described herein. The computer instructions may include, for example, routines, programs, subjects, components, data structures, procedures, modules, and functions, which perform particular functions described herein. For example, the processor 210 may process image data obtained from the RT device 110, the terminal(s) 130, the storage device 150, and/or any other component of the RT system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data obtained from one or more components of the RT system 100. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure. For example, the storage device 220 may store a program to be executed by the processing device 140 to estimate a radiation dose delivered to the subject. As another example, the storage device 220 may store a program to be executed by the processing device 140 to cause the treatment radiation source 117 to adjust its machine parameters including, for example, positions of jaws.

The I/O 230 may input and/or output signals, data, information, etc. In some embodiments, the I/O 230 may enable a user interaction with the processing device 140. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the processing device 140 and the RT device 110, the terminal(s) 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 according to some embodiments of the present disclosure. In some embodiments, one or more terminals 130 and/or a processing device 140 may be implemented on a mobile device 300, respectively.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™ Android™, Windows Phone™) and one or more applications 380 may be loaded into the memory 360 from the storage 390 in order to be executed by the CPU 340. The applications 380 may include a browser or any other suitable mobile apps for receiving and rendering information relating to the RT system 100. User interactions with the information stream may be achieved via the I/O 350 and provided to the processing device 140 and/or other components of the RT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
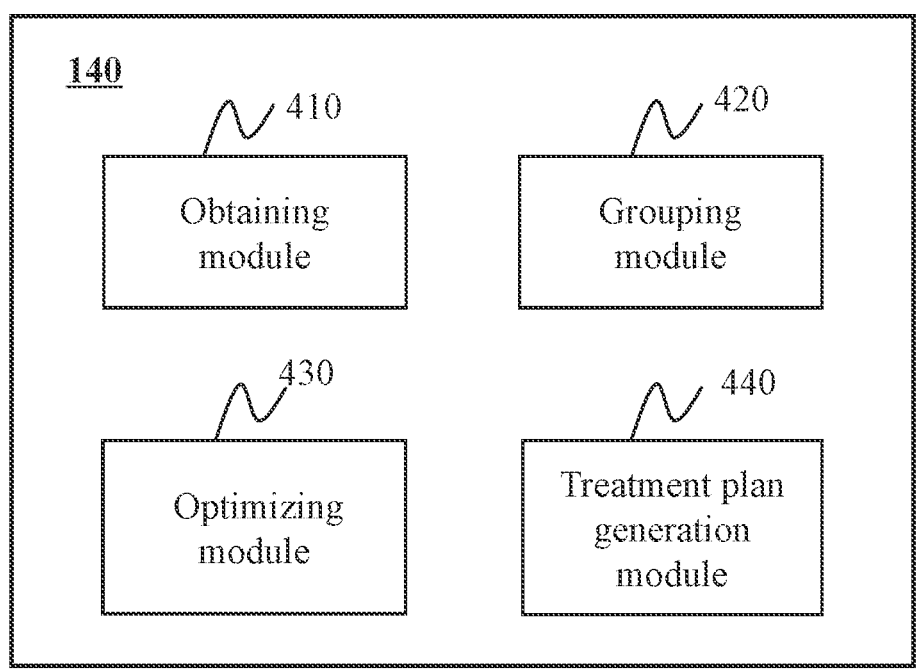
FIG. 4 is a block diagram illustrating an exemplary processing device according to some embodiments of the present disclosure.

FIG. 4 is a block diagram illustrating an exemplary processing device 140 according to some embodiments of the present disclosure. As shown in FIG. 4, the processing device 140 may include an obtaining module 410, a grouping module 420, an optimizing module 430, and a treatment plan generation module 440.

The obtaining module 410 may obtain data and/or information. The obtaining module 410 may obtain data and/or information from the RT device 110, the one or more terminals 130, the storage device 150, or any devices or components capable of storing data via the network 120. In some embodiments, the obtaining module 410 may obtain a plurality of beam angles of an arc for radiation treatment. Each of the plurality of beam angles may be associated with at least one control point, and each of the at least one control point may correspond to a segment shape formed by one or more pairs of leaves of a collimator and a segment weight. In some embodiments, the obtaining module 410 may further obtain preliminary segment parameters of control points associated with the plurality of beam angles. The preliminary segment parameters of each control point may include a preliminary segment shape and a preliminary segment weight.

The grouping module 420 may group the plurality of beam angles into at least two sets so that each pair of two consecutive beam angles of the plurality of beam angles to different sets of the at least two sets. For instance, the plurality of beam angles may include pairs of consecutive beam angles of ($A_{2n}$, $A_{2n+1}$) in which n is an integer equal to or larger than 0; the grouping module 420 may group the plurality of beam angles into at least two sets such that $A_{2n}$ and $A_{2n+1}$ belong to different sets of the at least two sets.

The optimizing module 430 may determine target segment parameters of the control points in each of the at least two sets by optimizing, based on a first leaf motion constraint and/or a second leaf motion constraint, the preliminary segment parameters of the control points associating with the plurality of beam angles. The target segment parameters of each control point may include a target segment shape and a target segment weight. The first leaf motion constraint may relate to a motion of a leaf of the collimator between a pair of consecutive beam angles among the plurality of beam angles. The second leaf motion constraint may relate to a motion of a leaf of the collimator between a pair of consecutive control points of a beam angle.

The treatment plan generation module 440 may generate a treatment plan (e.g., a VMAT treatment plan) based on the target segment parameters of the control points in each of the at least two sets. The treatment plan generation module 440 may determine configuration parameters of the treatment plan based on the target segment parameters of the control points in each of the at least two sets. The configuration parameters of the treatment plan may include, e.g., rotation angles of the gantry 118, moving distances of each of the leaves of the MLC between any two control points of the control points in the at least two sets during the treatment, etc. The treatment plan generation module 440 may generate the treatment plan based on the configuration parameters of the treatment plan.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 140 may include one or more other modules and/or one or more modules described above may be omitted. For example, the processing device 140 may include a storage module (not shown) used to store information and/or data associated with the VMAT treatment plan. Additionally or alternatively, two or more modules may be integrated into a single module and/or a module may be divided into two or more units. For example, the grouping module 420 and the optimizing module 430 may be combined into a processing module. However, those variations and modifications also fall within the scope of the present disclosure.

Figure 5:
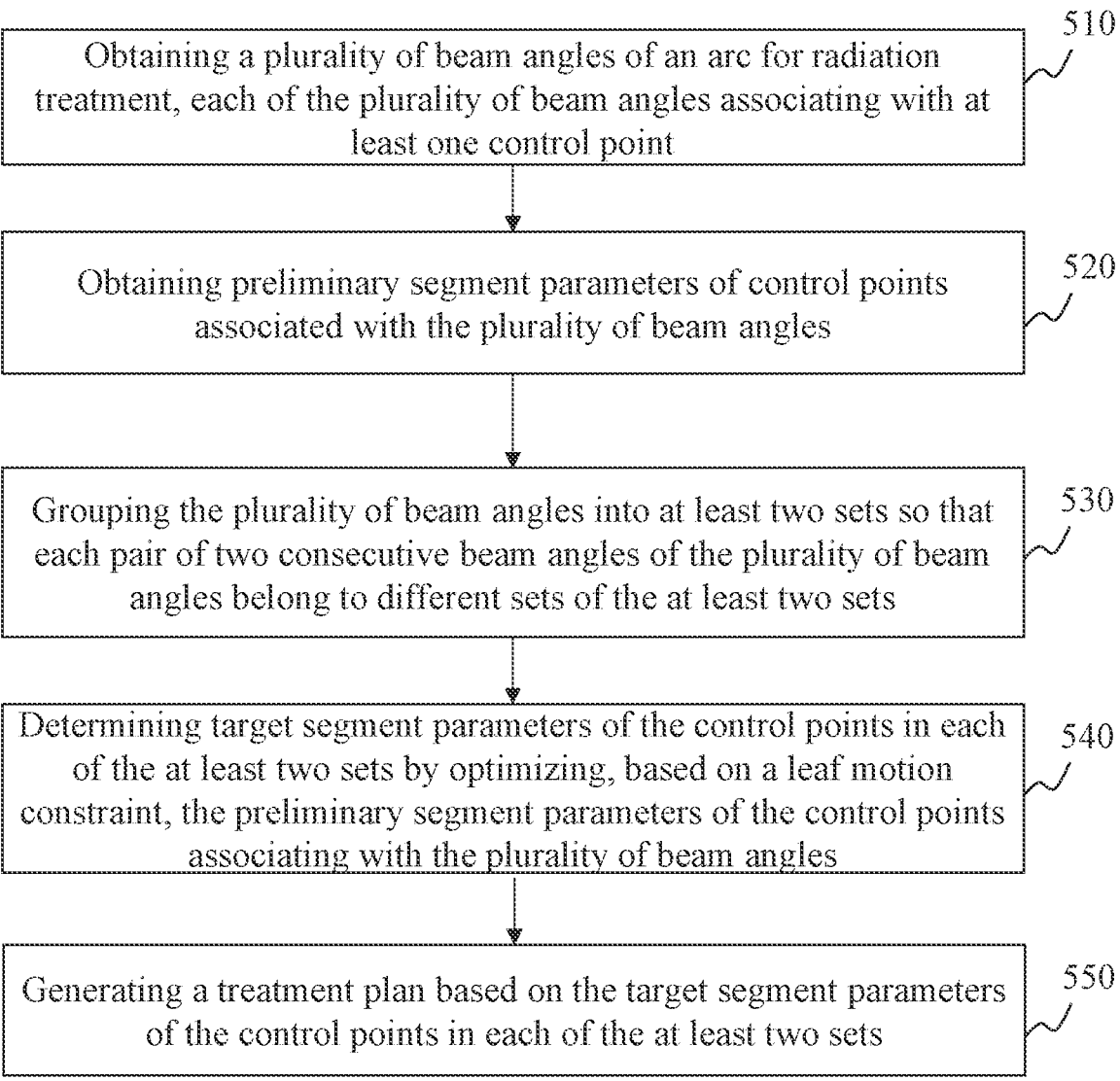
FIG. 5 includes a flowchart illustrating an exemplary process for generating a treatment plan according to some embodiments of the present disclosure.

FIG. 5 includes a flowchart illustrating an exemplary process for generating a treatment plan according to some embodiments of the present disclosure. In some embodiments, process 500 may be executed by the RT system 100. For example, the process 500 may be implemented as a set of instructions (e.g., an application) stored in a storage device (e.g., the storage device 150, the storage device 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 500.

In 510, the processing device 140 (e.g., the obtaining module 410) may obtain a plurality of beam angles of an arc for radiation treatment, each of the plurality of beam angles associating with at least one control point.

The treatment plan may be a treatment plan of, e.g., a VMAT treatment to be applied to a subject (e.g., a patient, tissue or an organ of a patient, etc.). The treatment plan may include a plurality of treatment parameters, such as a planned treatment duration, a planned radiation dose, a planned radiation energy delivery direction, a planned beam shape of a radiation beam, a planned cross-sectional area of the radiation beam, a planned field shape (e.g., a shape of a radiation filed on the subject), etc. The treatment plan may be made before the treatment is performed on the subject.

The VMAT treatment refers to a radiation treatment during which a treatment beam is emitted (e.g., continuously emitted) from the treatment radiation source 117 as the gantry 118 rotates around a rotation axis. The treatment beam may be a photon beam, an electron beam, a proton beam, a neutron beam, or the like, or any combination thereof. The treatment beam may pass through an aperture formed by the collimator assembly 119. In some embodiments, the collimator assembly 119 may include a multi-leaf collimator (MLC). The MLC may include one or more pairs of leaves. Positions of one or more of the multiple leaves may change dynamically to modulate radiation fields according to actual needs (e.g., a total radiation dose (e.g., 0.1 Gy, 1 Gy, 5 Gy, 10 Gy, 50 Gy, 100 Gy, etc.) and/or a dose distribution).

The treatment plan (e.g., VMAT treatment plan) may involve an arc for radiation treatment. The arc may be a moving trajectory of the treatment beam during the VMAT treatment. The arc may be a coplanar arc or a non-coplanar arc. The coplanar arc refers to an arc formed by fixing a couch rotation angle (i.e., a rotation angle of the couch 114) at zero degrees as the gantry 118 rotates during the VMAT treatment. The non-coplanar arc refers to an arc formed by fixing the couch rotation angle at a non-zero degree angle as the gantry 118 rotates during the VMAT treatment (i.e., a longitudinal direction of the couch 114 is not parallel to the rotation axis of the gantry 118).

The arc may correspond to an angle range. The angle range may be a range including multiple beam angles. A beam angle refers to an angle between the treatment beam and a reference direction. For example, a beam angle may be defined as an angle between a centerline of the treatment beam and the Z-axis of the coordinate system 160 as illustrated in FIG. 1. Merely by way of example, the arc may correspond to an angle range of 0-100 degrees. The processing device 140 may obtain the plurality of beam angles from the angle range. The plurality of beam angles may be discrete angles sampled from the angle range at a first interval. The first interval may be a constant or a variable. Merely by way of example, the plurality of beam angles may be discrete angles sampled at a constant interval (e.g., 10 degrees). The plurality of beam angles may be, for example, 0°, 10°, 20°, 30°, 40°, 50°, 60°, 70°, 80°, 90°, and 100°.

Each of the plurality of beam angles may be associated with at least one control point. Each of the at least one control point may be a node set on the arc for controlling a shape of the radiation field and a radiation intensity so as to improve an accuracy of the radiation dose delivered to the subject during the VMAT treatment. In some embodiments, each of the at least one control point may correspond to an angle that is equal to or in a vicinity of a beam angle. For example, the beam angle 10° may be associated with five control points which correspond to five angles. The five angles may include, for example, 6°, 8°, 10°, 12°, and 14°. The at least one control point may be represented by or referred to using the at least one angle for brevity in the present disclosure.

Each of the at least one control point may correspond to one or more segment parameters. The one or more segment parameters may include at least a segment shape and a segment weight. The segment shape at a control point may characterize a shape (e.g., a square, a circle, an ellipse, etc.) of a radiation field at the control point. The segment shape at the control point may be determined by an aperture formed by the one or more pairs of leaves of the MLC. The segment weight may characterize a radiation dose, a radiation intensity, a cumulative radiation dose, and/or a cumulative radiation intensity at the control point.

In 520, the processing device 140 (e.g., the obtaining module 410) may obtain preliminary segment parameters of control points associated with the plurality of beam angles.

The preliminary segment parameters refer to preliminary values of the segment parameters at the control points. The preliminary segment parameters of each control point may include a preliminary segment shape and a preliminary segment weight. The preliminary segment shape refers to a preliminary shape of the radiation field at the control point. The preliminary segment weight refers to a preliminary value of the segment weight at the control point.

The preliminary segment parameters of the control points may be generated in different ways. In some embodiments, the preliminary segment parameters of the control points may be set by a user, according to default settings of the RT system 100, etc. For example, a user may assign values as the preliminary segment parameters of the control points according to, e.g., historical values of the segment parameters of the control points. As another example, the RT system 100 may generate random numbers, and designate the random numbers as the preliminary segment parameters of the control points. As a further example, the preliminary segment parameters of the control points may be empirical values. In some embodiments, the preliminary segment parameters of the control points may be generated, using a leaf sequencing algorithm, based on fluence maps corresponding to the plurality of beam angles. The fluence maps may be generated based on a fluence map optimization (FMO) algorithm. In some embodiments, the preliminary segment parameters of the control points may be generated based on a direct aperture optimization (DAO) algorithm.

In some embodiments, the processing device 140 may determine target segment parameters of the control points by a target parameter determination process. In some embodiments, the target parameter determination process may include grouping the plurality of beam angles into at least two sets as illustrated in 530 and determining the target segment parameters of the control points in each of the at least two sets by optimizing, based on a leaf motion constraint, the preliminary segment parameters of the control points associating with the plurality of beam angles as illustrated in 540.

In 530, the processing device 140 (e.g., the grouping module 420) may group the plurality of beam angles into at least two sets so that each pair of two consecutive beam angles of the plurality of beam angles belong to different sets of the at least two sets. For instance, the plurality of beam angles may include pairs of consecutive beam angles of $(A_{2n}, A_{2n+1})$ in which n is an integer equal to or larger than 0; the processing device 140 (e.g., the grouping module 420) may group the plurality of beam angles into at least two sets such that $A_{2n}$ and $A_{2n+1}$ belong to different sets of the at least two sets.

As used herein, a pair of two consecutive beam angles may be two neighboring beam angles among the plurality of beam angles such that no other beam angle of the plurality of beam angles exists between the pair of two consecutive beam angles. Each of the at least two sets may include at least one control point.

Merely for illustration, referring to the above example where the plurality of beam angles include 0°, 10°, 20°, 30°, 40°, 50°, 60°, 70°, 80°, 90°, and 100°, beam angles such as 0° and 10°, 10° and 20°, 20° and 30°, 30° and 40°, etc., belong to a pair of two consecutive beam angles. The beam angles may be grouped into two sets including an 11th set and a 12th set. The 11th set may include beam angles 0°, 20°, 40°, 60°, 80°, and 100°. The 12th set may include beam angles 10°, 30°, 50°, 70°, and 90°. As another example, the beam angles may be grouped into three sets including a 21th set, a 22th set, and a 23th set. The 21th set may include beam angles 0°, 30°, 60°, 90°. The 22th set may include beam angles 10°, 40°, 70°, and 100°. The 23th set may include beam angles 20°, 50°, 80°. It should be noted that the above examples regarding the grouping of the plurality of beam angles are merely provided for illustration purposes and not intended to be limiting.

After the plurality of beam angles are grouped into the at least two sets, the control points associated with the plurality of beam angles may also be grouped into the at least two sets. For example, the beam angle 10° may be grouped into the 12th set, and control points 6°, 8°, 10°, 12°, and 14° may also be grouped into the 12th set.

In 540, the processing device 140 (e.g., the optimizing module 430) may determine target segment parameters of the control points in each of the at least two sets by optimizing, based on a leaf motion constraint, the preliminary segment parameters of the control points associating with the plurality of beam angles.

The target segment parameters of each control point may include a target segment shape and a target segment weight. The target segment shape refers to a target shape of the radiation field at the control point. The target segment weight refers to a target value of the segment weight at the control point.

As used herein, the leaf motion constraint refers to a constraint relating to a motion of each of at least one leaf of the MLC during the treatment (e.g., the VMAT treatment). The leaf motion constraint may include a first leaf motion constraint and/or a second leaf motion constraint. As used herein, the first leaf motion constraint refers to a constraint relating to a motion of each of at least one leaf of the MLC between a pair of consecutive beam angles among the plurality of beam angles. In some embodiments, the first leaf motion constraint may define an upper limit of a moving distance of each of at least one leaf of the MLC between a pair of consecutive beam angles among the plurality of beam angles. The first leaf motion constraint may mainly be determined by a performance of hardware of the RT system 100 (e.g., the gantry 118 and/or the leaves of the MLC). In some embodiments, the first leaf motion constraint may be a constraint defining a motion of each of at least one leaf of the MLC between a last control point associated with a former beam angle and a first control point associated with a latter beam angle immediately following the former beam angle. The former beam angle and the latter beam angle may be a pair of consecutive beam angles among the plurality of beam angles. Merely by way example, the former beam angle may be 10°. The former beam angle may be associated with control points of 6°, 8°, 10°, 12°, and 14°. The last control point associated with the former beam angle may be 14°. The latter beam angle may be 20°. The latter beam angle may associate with control points of 16°, 18°, 20°, 22°, and 24°. The first control point associated with the latter beam angle may be 16°. The first leaf motion constraint may define an upper limit of a moving distance of each of at least one leaf of the MLC between the control points 14° and 16°. The second leaf motion constraint refers to a constraint relating to a motion of each of at least one leaf of the MLC between a pair of consecutive control points associated with a same beam angle. In some embodiments, the second leaf motion constraint may define an upper limit of a moving distance of each of at least one leaf of the MLC between a pair of consecutive control points associated with a beam angle. For example, control points associated with a first beam angle may include 10°, 11°, and 12°, and control points associated with a second beam angle may include 13°, 14°, and 15°. Correspondingly, the first leaf motion constraint may define an upper limit of a moving distance of each of at least one leaf of the MLC between, for example, 12° and 13°, and the second leaf motion constraint may define an upper limit of a moving distance of each of at least one leaf of the MLC between, for example, 10° and 11°, 11° and 12°, 13° and 14°, and/or 14° and 15°.

The processing device 140 may determine the target segment parameters of the control points in each of the at least two sets by optimizing, based on the first leaf motion constraint, the preliminary segment parameters of the control points associated with the plurality of beam angles. The optimization of the preliminary segment parameters may be implemented using a fluence map optimization algorithm, a DAO algorithm, etc., which is provided for illustration purposes and not intended to be limiting. More descriptions regarding the optimization of the preliminary segment parameters can be found elsewhere in the present disclosure. See, for example, FIGS. 6-8 and the descriptions thereof.

In some embodiments, the target segment parameters of the control points in each of the at least two sets may be determined by optimizing, based on the first leaf motion constraint and the second leaf motion constraint, the preliminary segment parameters of the control points associated with the plurality of beam angles. By optimizing the preliminary segment parameters of the control points associated with the plurality of beam angles based on the first leaf motion constraint and the second leaf motion constraint, the target segment parameters of the control points may satisfy both the first leaf motion constraint and the second leaf motion constraint at the same time, thus improving the optimization efficiency and/or accuracy of the segment parameters of the control points and enhancing the efficacy of the VMAT treatment.

In some embodiments, the target segment parameters of the control points in each of the at least two sets may be determined by optimizing the preliminary segment parameters of the control points in the at least two sets in sequence based on the first leaf motion constraint and the second leaf motion constraint. When preliminary segment parameters of control points in one of the at least two sets are optimized, current segment parameters of control points in other sets of the at least two sets may remain unchanged. As used herein, current segment parameters refer to current values of the segment parameters at the control points. The current segment parameters of each control point may include a current segment shape and a current segment weight. The current segment shape refers to a current shape of the radiation field at the control point. The current segment weight refers to a current value of the segment weight at the control point. For a control point, if the segment parameters at the control point are not optimized yet, the current segment parameters of the control point may be preliminary segment parameters of the control point; if the segment parameters at the control point have been optimized, the current segment parameters of the control point may be optimized segment parameters of the control point.

Preliminary segment parameters of the control points in one set of the at least two sets may be optimized each time during the optimization process. For example, referring to the above example where the plurality of beam angles include 0°, 10°, 20°, 30°, 40°, 50°, 60°, 70°, 80°, 90°, and 100°, the 11 beam angles may be grouped into two sets including the 11th set and the 12th set. The 11th set may include beam angles 0°, 20°, 40°, 60°, 80°, and 100°. The 12th set may include beam angles 10°, 30°, 50°, 70°, and 90°. During the optimization process, preliminary segment parameters of the control points in the 11th set may be optimized at first based on the first leaf motion constraint, the second leaf motion constraint, and preliminary segment parameters of the control points in the 12th set. When preliminary segment parameters of control points in the 11th set are being optimized, the preliminary segment parameters of the control points in the 12th set may remain unchanged. Then the preliminary segment parameters of the control points in the 12th set may be optimized based on the first leaf motion constraint, the second leaf motion constraint, and the optimized preliminary segment parameters (also referred to as optimized segment parameters) of the control points in the 11th set. As set forth above, preliminary segment parameters of the control points in the two sets may be optimized in sequence until the target segment parameters of the control points in each of the two sets are determined. By keeping the current segment parameters of control points in other sets of the at least two sets unchanged when preliminary segment parameters of control points in one of the at least two sets are being optimized, a count (or number) of variables may be reduced in the optimization each time, a convergency of the optimization may be reached more easily, and the efficiency of the optimization may also be improved.

In some embodiments, the target segment parameters of the control points in each of the at least two sets may be determined by optimizing the preliminary segment parameters of the control points in two or more of the at least two sets simultaneously based on the first leaf motion constraint and the second leaf motion constraint. Referring to the above example where the plurality of beam angles include 0°, 10°, 20°, 30°, 40°, 50°, 60°, 70°, 80°, 90°, and 100°, the 11 beam angles may be grouped into four sets including a 31th set, a 32th set, a 33th set, and a 34th set. The 31th set may include beam angles 0°, 40°, and 80°. The 32th set may include beam angles 10°, 50°, and 90°. The 33th set may include beam angles 20°, 60°, and 100°. The 34th set may include beam angles 30° and 70°. Preliminary segment parameters of the control points in the 32th set and the 34th set may be optimized at first based on the first leaf motion constraint, the second leaf motion constraint, and preliminary segment parameters of the control points in the 31th set and the 33th set. Then preliminary segment parameters of the control points in the 31th set and 33th set may be optimized based on the first leaf motion constraint, the second leaf motion constraint, and the optimized segment parameters of the control points in the 32th set and the 34th set. As set forth above, preliminary segment parameters of the control points in two sets may be optimized simultaneously until the target segment parameters of the control points in each of the four sets are determined.

In 550, the processing device 140 (e.g., the treatment plan generation module 440) may generate a treatment plan based on the target segment parameters of the control points in each of the at least two sets.

The processing device 140 may determine configuration parameters of the treatment plan (e.g., VMAT treatment plan) based on the target segment parameters of the control points in each of the at least two sets. The configuration parameters of the treatment plan may include, e.g., rotation angles of the gantry 118, moving distances of each of the one or more pairs of leaves of the MLC between any two control points of the control points in the at least two sets during the treatment, etc. The processing device 140 may generate the treatment plan based on the configuration parameters of the treatment plan.

According to the embodiments set forth above, the target segment parameters of the control points in each of the at least two sets may be generated under the first leaf motion constraint. In the optimization process, the plurality of beam angles may be grouped into the at least two sets and the control points associated with the plurality of beam angles may also be grouped into the at least two sets together with the plurality of beam angles. The preliminary segment parameters of the control points in the at least two sets may be optimized simultaneously or in sequence based on the first leaf motion constraint and/or the second leaf motion constraint. The entire optimization process of the preliminary segment parameters may be separated into multiple fractions. In each of the multiple fractions, preliminary segment parameters of control points in one or more sets of the at least two sets may be optimized each time. In this way, a count (or number) of variables may be reduced in each fraction and a convergency of the optimization may be reached more easily. More attention may be paid to fractions having poor optimization effect, instead of all the multiple fractions, and the efficiency of the optimization may also be improved. In the meanwhile, by performing the optimization based on the first leaf motion constraint and/or the second leaf motion constraint, the motion of one or more pairs of leaves of the MLC may be optimized to reduce or minimize the motion of the leaves during the execution of a treatment plan (e.g., VMAT treatment plan) so acquired, and/or improve the conformity of an actual radiation delivery to the treatment plan. Accordingly, the target segment parameters of the control points may be set such that an execution time of the treatment is relatively short. Thus, a treatment performed according to the generated treatment plan may achieve a better efficacy within a short execution time.

In some embodiments, the preliminary segment parameters of the control points of the plurality of beam angles may be determined based on the second leaf motion constraint. In some embodiments, the preliminary segment parameters of the control points may be determined, using a leaf sequencing algorithm, based on fluence maps corresponding to the plurality of beam angles and the second leaf motion constraint. The fluence maps may be generated based on a fluence map optimization (FMO) algorithm. In some embodiments, the preliminary segment parameters of the control points may be generated based on a direct aperture optimization (DAO) algorithm and the second leaf motion constraint. By determining the preliminary segment parameters of the control points based on the second leaf motion constraint, the preliminary segment parameters of the control points may meet the requirements for the motion of each of at least one leaf of the MLC between a pair of consecutive control points associated with a same beam angle before the optimization process starts, which may improve the optimization efficiency.

Figure 6:
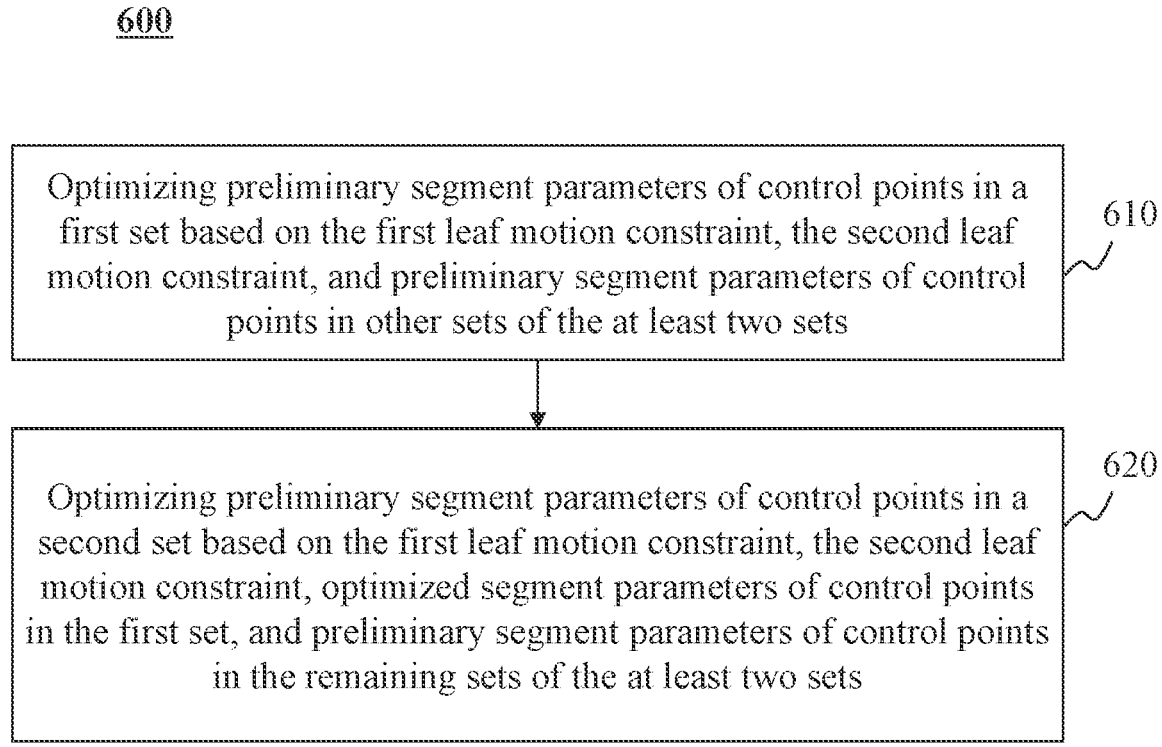
FIG. 6 includes a flowchart illustrating an exemplary process for optimizing the preliminary segment parameters of the control points of the plurality of beam angles according to some embodiments of the present disclosure.

FIG. 6 includes a flowchart illustrating an exemplary process for optimizing the preliminary segment parameters of the control points of the plurality of beam angles according to some embodiments of the present disclosure. In some embodiments, process 600 may be executed by the RT system 100. For example, the process 600 may be implemented as a set of instructions (e.g., an application) stored in a storage device (e.g., the storage device 150, the storage device 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 600. In some embodiments, the operation in 540 of the process 500 in FIG. 5 may be performed according to the process 600.

In 610, the processing device 140 (e.g., the optimizing module 430) may optimize preliminary segment parameters of control points in a first set based on the first leaf motion constraint, the second leaf motion constraint, and preliminary segment parameters of control points in other sets of the at least two sets.

The first set may be selected from the at least two sets generated in 530 of the process 500 by a user (e.g., a doctor, a technician, etc.) or the processing device 140. For example, the processing device 140 may designate any one set from the at least two sets as the first set. Optimized segment parameters of control points in the first set may be determined by optimizing the preliminary segment parameters of control points in the first set based on the first leaf motion constraint, the second leaf motion constraint, and preliminary segment parameters of control points in other sets of the at least two sets except the first set. The optimization of the preliminary segment parameters may be implemented using a fluence map optimization algorithm, a DAO algorithm, etc. When preliminary segment parameters of control points in the first set are being optimized, preliminary segment parameters of control points in the other set may remain unchanged.

In 620, the processing device 140 (e.g., the optimizing module 430) may optimize preliminary segment parameters of control points in a second set based on the first leaf motion constraint, the second leaf motion constraint, optimized segment parameters of control points in the first set, and preliminary segment parameters of control points in the remaining set(s) of the at least two sets other than the first set that has been optimized as described in 610 and the second set that is being optimized.

After the optimized segment parameters of the control points in the first set are determined, the second set may be selected from the other set of the at least two sets by a user or the processing device 140. For example, the processing device 140 may any one set other than the first set from the at least two sets as the second set.

A remaining set refers to a set of control points of the at least two sets other than any set that has been optimized as described in 610 (e.g., the first set in the description of FIG. 6) and any set that is being optimized (e.g., the second set in the description of FIG. 6). If a count (or number) of the at least two sets is two, there is no remaining set of the at least two sets other than the first set that has been optimized as described in 610 and the second set that is being optimized as exemplified in FIG. 6. Preliminary segment parameters of the control points in the second set may be optimized based on the first leaf motion constraint, the second leaf motion constraint, and the optimized segment parameters of the control points in the first set. If the count (or number) of the at least two sets exceeds two, the preliminary segment parameters of the control points in the second set may be optimized based on the first leaf motion constraint, the second leaf motion constraint, the optimized segment parameters of the control points in the first set, and preliminary segment parameters of control points in the remaining set(s) of the at least two sets.

Further, the preliminary segment parameters of the control points in each of the remaining sets of the at least two sets may be optimized in sequence. The optimization process may terminate until the preliminary segment parameters of the control points in each of the at least two sets are optimized.

Merely for illustration purposes, referring to the above example where the plurality of beam angles include 0°, 10°, 20°, 30°, 40°, 50°, 60°, 70°, 80°, 90°, and 100°, the 11 beam angles may be grouped into four sets including a 31th set, a 32th set, a 33th set, and a 34th set. During the in sequence optimization process, preliminary segment parameters of the control points in the 34th set may be optimized in a first fraction of the optimization process based on the first leaf motion constraint, the second leaf motion constraint, and preliminary segment parameters of the control points in the 31th set, the 32th set, and the 33th set. When preliminary segment parameters of control points in the 34th set are being optimized, preliminary segment parameters of control points in the 31th set, the 32th set, and the 33th set may remain unchanged. In this way, a count (or number) of variables may be reduced in each fraction and a convergency of the optimization may be reached more easily. More attention may be paid to fractions having poor optimization effect, instead of all the multiple fractions, and the efficiency of the optimization may also be improved. In a second fraction of the optimization process, preliminary segment parameters of the control points in the 31th set may be optimized based on the first leaf motion constraint, the second leaf motion constraint, preliminary segment parameters of the control points in the 32th set and the 33th set, and the optimized segment parameters of the control points in the 34th set. Preliminary segment parameters of the control points in the 32th set and/or the 33th set may be optimized similarly. The optimization process may terminate until preliminary segment parameters of the control points in each of the four sets are optimized, and the target segment parameters of the control points in each of the four sets may be determined.

Figure 7:
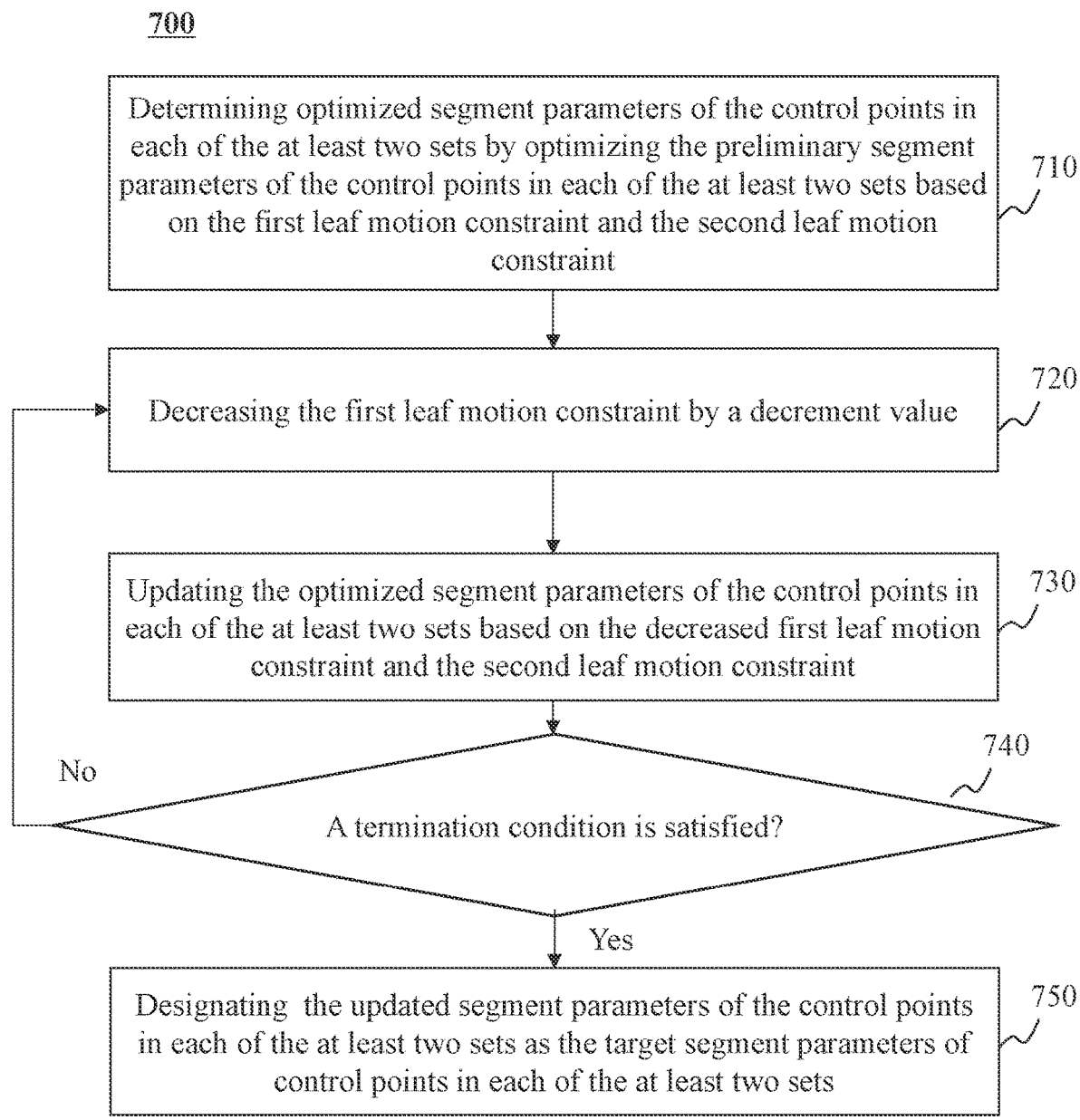
FIG. 7 includes a flowchart illustrating an exemplary process for optimizing the preliminary segment parameters of the control points of the plurality of beam angles according to some embodiments of the present disclosure.

FIG. 7 includes a flowchart illustrating an exemplary process for optimizing the preliminary segment parameters of the control points of the plurality of beam angles according to some embodiments of the present disclosure. In some embodiments, process 700 may be executed by the RT system 100. For example, the process 700 may be implemented as a set of instructions (e.g., an application) stored in a storage device (e.g., the storage device 150, the storage device 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 700. In some embodiments, the operation 540 of the process 500 in FIG. 5 may be performed according to the process 700.

In 710, the processing device 140 (e.g., the optimizing module 430) may determine optimized segment parameters of the control points in each of the at least two sets by optimizing the preliminary segment parameters of the control points in each of the at least two sets based on the first leaf motion constraint and the second leaf motion constraint.

In some embodiments, the first leaf motion constraint may be set by a user, according to default settings of the RT system 100, etc. For example, a user may assign a relatively large value (e.g., a value that the motion of the one or more pairs of leaves of the MLC may satisfy easily) as the first leaf motion constraint according to, e.g., historical values of the first leaf motion constraint. As another example, the first leaf motion constraint may be set automatically according to empirical values, such as 10 millimeters (mm), 5 mm, etc. In some embodiments, the second leaf motion constraint may also be set by a user, according to default settings of the RT system 100, etc. In some embodiments, the second leaf motion constraint may be smaller than or equal to the first leaf motion constraint. Merely by way of example, the second leaf motion constraint may equal the first leaf motion constraint.

The preliminary segment parameters of the control points in each of the at least two sets may be optimized, based on the first leaf motion constraint and the second leaf motion constraint. The optimization may be performed using the fluence map optimization algorithm, the DAO algorithm, etc. The optimized preliminary segment parameters of the control points in each of the at least two sets may be referred to as the optimized segment parameters of the control points in the set of the at least two sets.

In 720, the processing device 140 (e.g., the optimizing module 430) may decrease the first leaf motion constraint by a decrement value.

The decrement value may be set by a user, according to default settings of the RT system 100, etc. In some embodiments, the decrement value may be set according to actual needs. Merely by way of example, the decrement value may be 1 millimeter (mm), 2 mm, 3 mm, etc. The first leaf motion constraint may be decreased by the decrement value.

In 730, the processing device 140 (e.g., the optimizing module 430) may update the optimized segment parameters of the control points in each of the at least two sets based on the decreased first leaf motion constraint and the second leaf motion constraint.

The decreased first leaf motion constraint may be regarded as a new first leaf motion constraint. The processing device 140 may update the optimized segment parameters of the control points in each of the at least two sets based on the new first leaf motion constraint and the second leaf motion constraint. The updating of the optimized segment parameters of the control points may be implemented using the fluence map optimization algorithm, the DAO algorithm, etc. The updated optimized segment parameters may also be referred to as updated segment parameters.

In 740, the processing device 140 (e.g., the optimizing module 430) may determine whether a termination condition is satisfied.

In some embodiments, the termination condition may include that the decreased first leaf motion constraint is equal to a target constraint. The target constraint may be set by a user, according to default settings of the RT system 100, etc. Merely by way of example, the target constraint may be 2 mm, 3 mm, 5 mm, etc. In some embodiments, the second leaf motion constraint may equal the target constraint. The first leaf motion constraint may be a specific multiple (larger than or equal to 1) of the target constraint. The specific multiple may be larger than or equal to 1. For example, the first leaf motion constraint may be 1.2 times, 1.5 times, 4 times, 8 times, 16 times, etc., of the target constraint. If the decreased first leaf motion constraint is equal to the target constraint, indicating that a termination condition is satisfied, the process 700 may proceed to 750. In some embodiments, such a termination condition may relate to a requirement for the motion of each of the one or more pairs of leaves of the MLC when segment shapes defined by the updated segment parameters are formed. As illustrated in FIG. 7, the process 700 may include an iterative process including one or more iterations. In each of the one or more iterations, the operations in 720 through 740 are performed. The iterative process may terminate when the decreased first leaf motion constraint obtained in the latest iteration of the one or more iterations is equal to the target constraint.

In some embodiments, in 740 if the decreased first leaf motion constraint is determined to be smaller than the target constraint, and the updated segment parameters are determined under the decreased first leaf motion constraint but not the target constraint, the decreased first leaf motion constraint may be adjusted to the target constraint. The processing device 140 may determine third optimized segment parameters of control points in each of the at least two sets based on the adjusted first leaf motion constraint (i.e., the target constraint) and the second leaf motion constraint. The third optimized segment parameters of the control points in each of the at least two sets may be designated as the target segment parameters of the control points in each of the at least two sets. The third optimized segment parameters of the control points refer to third values of the segment parameters of the control points generated by optimizing the segment parameters of the control points through adjusting the decreased first leaf motion constraint (smaller than the target constraint) to the target constraint. In this way, the optimized segment parameters of the control points may be updated under a more reasonable leaf motion constraint, which may improve the optimization effect and/or enhance the efficacy of the VMAT treatment performed according to the VMAT treatment plan including the target segment parameters of control points in each of the at least two sets so determined.

If the decreased first leaf motion constraint is larger than the target constraint, the process 700 may return to 720 to initiate a next iteration of the one or more iterations. If the decreased first leaf motion constraint exceeds the target constraint, it may indicate that the optimization does not meet the requirement for the motion of each of the one or more pairs of leaves of the MLC when segment shapes defined by the updated segment parameters are formed. The updated segment parameters of the control points in each of the at least two sets may not be used in a VMAT treatment. In such a case, a next iteration may be performed in which the new first leaf motion constraint may further be decreased by the decrement value and the updated segment parameters may be further optimized based on the new first leaf motion constraint and the second motion constraint.

In some embodiments, in each of the one or more iterations, the processing device 140 may further regroup the plurality of beam angles into multiple sets such that each pair of two consecutive beams angles of the plurality of beam angles belong to different sets of the multiple sets, and determine second optimized segment parameters of the control points in each of the multiple sets based on the decreased first leaf motion constraint, the second leaf motion constraint, and the updated segment parameters of the control points of the plurality of beam angles. The second optimized segment parameters of the control points refer to second values of the segment parameters of the control points generated by optimizing the segment parameters of the control points through the regrouping operation. In some embodiments, the regrouping of the plurality of beam angles may be performed according to the operations of the process 800 as illustrated in FIG. 8. The sets of the plurality of beam angles determined in different grouping or regrouping operations may be different. That is, the grouping as described in FIG. 5 and one or more regrouping as described in FIG. 7 may be performed according to at least two different grouping/regrouping rules. A grouping/regrouping rule may specify how to assign the plurality of beam angles to multiple sets and/or how many beam angles in each set.

In some embodiments, the termination condition may include at least one of the decreased first leaf motion constraint is smaller than or equal to the target constraint, a preset number or count of iterations are performed, or a radiation dose at each control point is within a preset dose range. The preset number or count of iterations may be set by a user, according to default settings of the RT system 100, etc. For example, the preset number or count may be 10, 20, 30, 40, 50, 100, 200, etc. Details regarding the radiation dose at each control point may be found elsewhere in the present disclosure, which is not repeated here.

In 750, the processing device 140 (e.g., the optimizing module 430) may designate the updated segment parameters of the control points in each of the at least two sets as the target segment parameters of control points in each of the at least two sets. The VMAT treatment plan including the target segment parameters of control points in each of the at least two sets may be obtained. The target segment parameters of the control points in each of the at least two sets may be used in a VMAT treatment performed according the VMAT treatment plan.

By decreasing the first leaf motion constraint gradually, and updating the optimized segment parameters iteratively, the optimization effect may be improved. Also, the shapes of the radiation fields may better conform to those defined according to the VMAT treatment plan, thus enhancing the treatment efficacy of the VMAT treatment performed accordingly.

It should be noted that the above description is merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure. For example, the process 700 include decreasing the first leaf motion constraint by a decrement value in 720; and determining whether a termination condition (e.g., the first leaf motion constraint is smaller than the target constraint) is satisfied in 730. If the termination condition is satisfied, the optimized segment parameters of the control points in each of the at least two sets may be designated as the target segment parameters of the control points in each of the at least two sets. If the termination condition is not satisfied, the optimized segment parameters of the control points in each of the at least two sets may be updated based on the decreased first leaf motion constraint and the second leaf motion constraint in 740 and one or more iterations may be initiated until the termination condition is satisfied. In each of the one or more iterations, the decreased first leaf motion constraint may be further decreased by the decrement value in 720, and a determination as to whether the termination condition is satisfied in 730. If the termination condition is satisfied, the updated segment parameters of the control points in each of the at least two sets generated in a prior iteration may be designated as the target segment parameters of the control points in each of the at least two sets. If the termination condition is not satisfied, the updated segment parameters of the control points in each of the at least two sets may be further updated based on the further decreased first leaf motion constraint and the second leaf motion constraint in 740. Then a next iteration may be initiated.

FIG. 8 includes a flowchart illustrating an exemplary process for optimizing the preliminary segment parameters of the control points of the plurality of beam angles according to some embodiments of the present disclosure. In some embodiments, process 800 may be executed by the RT system 100. For example, the process 800 may be implemented as a set of instructions (e.g., an application) stored in a storage device (e.g., the storage device 150, the storage device 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 800. In some embodiments, the operation 540 of the process 500 in FIG. 5 may be performed according to the process 800.

In 810, the processing device 140 (e.g., the optimizing module 430) may determine optimized segment parameters of the control points in each of the at least two sets by optimizing, based on the first leaf motion constraint and the second leaf motion constraint, the preliminary segment parameters of the control points in each of the at least two sets.

The optimized segment parameters of the control points in each of the at least two sets may be determined by optimizing, based on the first leaf motion constraint and the second leaf motion constraint, preliminary segment parameters of the control points in each of the at least two sets using the fluence map optimization algorithm, the DAO algorithm, etc. In some embodiments, the operation in 810 may be the same as or similar to the operation in 710 of the process 700 as illustrated in FIG. 7, the description of which is not repeated here.

In 820, the processing device 140 (e.g., the optimizing module 430) may regroup the plurality of beam angles into multiple sets so that each pair of two consecutive beams angles of the plurality of beam angles belong to different sets of the multiple sets.

In some embodiments, a count (or number) of the multiple sets may be different from a count (or number) of the at least two sets generated in 530. For example, the plurality of beam angles including 0°, 10°, 20°, 30°, 40°, 50°, 60°, 70°, 80°, 90°, and 100° may be grouped into two groups including an 11th set and a 12th set in 530. The 11th set may include beam angles 0°, 20°, 40°, 60°, 80°, and 100°. The 12th set may include beam angles 10°, 30°, 50°, 70°, and 90°. By performing the regrouping operation, the plurality of beam angles may be regrouped into three sets including a 21th set, a 22th set, and a 23th set. The 21th set may include beam angles 0°, 30°, 60°, 90°. The 22th set may include beam angles 10°, 40°, 70°, and 100°. The 23th set may include beam angles 20°, 50°, 80°. In some embodiments, the plurality of beam angles may be regrouped into the multiple sets in a way similar to the operation in 530 of the process 500 as illustrated in FIG. 5.

In some embodiments, the combination of 810 and 820 may be iteratively performed. In each of one or more second iterations, 810 may be performed in which the plurality of beam angles may be regrouped into multiple sets such that each pair of two consecutive beams angles of the plurality of beam angles belong to different sets of the multiple sets, and 820 may be performed in which the target segment parameters of the control points may be determined by iteratively determining, based on the first leaf motion constraint, the second leaf motion constraint, and the preliminary segment parameters of the control points of the plurality of beam angles or optimized segment parameters in each of the multiple sets that are obtained in a prior second iteration operation. After each of the one or more second iterations are performed, the processing device 140 may determine whether a preset condition is satisfied. The preset condition may be the same as or similar to the termination condition as described above in FIG. 7. For example, the preset condition may include at least one of the decreased first leaf motion constraint is smaller than or equal to the target constraint, a preset number or count of iterations are performed, or a radiation dose at each control point is within a preset dose range.

In 830, the processing device 140 (e.g., the optimizing module 430) may determine second optimized segment parameters of control points in each of the multiple sets based on the first leaf motion constraint, the second leaf motion constraint, and the optimized segment parameters of the control points of the plurality of beam angles.

In some embodiments, the second optimized segment parameters of control points in each of the multiple sets may be determined in a way similar to the operation in 540 of the process 500, the description of which is not repeated here. In some embodiments, when the second optimized segment parameters of control points in each of the multiple sets are determined, the first leaf motion constraint may remain unchanged. For example, the first leaf motion constraint may be equal to or smaller than the target constraint. By setting a relatively small value for the first leaf motion constraint, the optimization efficiency and effect of the preliminary segment parameters of the control points in the multiple sets may be improved. Besides, only the plurality of beam angles may be regrouped into the multiple sets in the optimization process, and the first leaf motion constraint may remain unchanged, thus improving the optimization efficiency.

In some embodiments, after the optimized segment parameters of the control points are further optimized and the first leaf motion constraint achieves the target constraint (e.g., the first leaf motion constraint being equal to or smaller than the target constraint), the processing device 140 may further determine whether a radiation dose at each control point is within a preset dose range based on the optimized segment parameters of the control points in each set (e.g., each of the at least two sets obtained in 530 or the multiple sets obtained in 820). If the radiation dose at each control point is within the preset dose range, the optimized segment parameters of the control points in each set may be determined as the target segment parameters of the control points in each set.

If the radiation dose of at least one control point exceeds the preset dose range, the optimized segment parameters of the control points in each set may be further updated according to one or more segment parameter updating approaches. In some embodiments, the radiation dose at each control point may be determined according to a dose calculation algorithm including, e.g., the Monte Carlo algorithm, the pencil beam algorithm, the convolution algorithm, etc. Merely for illustration, the optimized segment parameters of the control points in each set may be further updated according to the following segment parameter updating approaches.

In a first segment parameter updating approach, the plurality of beam angles may further be regrouped into new sets. The optimized segment parameter of the control points in each of the new sets may be further updated based on the first leaf motion constraint and the second leaf motion constraint.

In a second segment parameter updating approach, the first leaf motion constraint may be further decreased (e.g., to a value lower than the target constraint). The optimized segment parameter of the control points in each set (e.g., each of the at least two sets obtained in 530 or the multiple sets obtained in 820) may be further updated based on the decreased first leaf motion constraint and the second leaf motion constraint.

In a third segment parameter updating approach, the plurality of beam angles may further be regrouped into new sets and the first leaf motion constraint may be further decreased at the same time (i.e., the third segment parameter updating approach including a combination of the first segment parameter updating approach and the second segment parameter updating approach). The optimized segment parameter of the control points in each of the new sets may be further updated based on the decreased first leaf motion constraint and the second leaf motion constraint.

In a fourth segment parameter updating approach, a user intervention may be needed. For example, a user may check and/or adjust one or more optimization configurations (e.g., the optimized segment parameters of the control points in at least one set, a decrement value of the first leaf motion constraint, etc.). The optimized segment parameter of the control points in each of the new sets may be further updated based on the adjusted one or more optimization configurations.

In some embodiments, one or more of the exemplified segment parameter updating approaches may be used to update the optimized segment parameters of the control points in each set until the radiation dose at each control point is within the preset dose range. By determining whether the radiation dose at each control point is within the preset dose range based on the optimized segment parameters of the control points in each set, the reliability of the optimization result may be improved.

In some embodiments, an optimization objective for a VMAT treatment to be performed according to a VMAT treatment plan may be determined according to Equation (1):

$$Obj = \Sigma_i \max(d_i - u_i, 0)^2 + \min(d_i - l_i, 0)^2, \quad (1)$$

where Obj denotes the optimization objective of radiation doses in the VMAT treatment, i denotes an i-th sampling point (e.g., a control point), $d_i$ denotes a radiation dose of the i-th sampling point, $u_i$ denotes an upper limit of the radiation dose at the i-th sampling point, and $l_i$ denotes a lower limit of the radiation dose at the i-th sampling point. The parameter $d_i$ may be determined based on a flux graph.

In some embodiments, the target segment parameters of the control points may be further optimized, for example, using a direct machine parameter optimization (DMPO) algorithm. A derivation of the optimization objective with respect to positions of one or more pairs of leaves of the MLC may be determined according to Equation (2):

$$\frac{\partial Obj}{\partial x_{cj}} = \Sigma_i \frac{\partial Obj}{\partial d_i} * \frac{\partial d_i}{x_{cj}}, \quad (2)$$

and a derivation of the optimization objective with respect to radiation energy of the treatment beam may be determined according to Equation (3):

$$\frac{\partial Obj}{\partial w_c} = \Sigma_i \frac{\partial Obj}{\partial d_i} * \frac{\partial d_i}{w_c}, \quad (3)$$

where $x_{cj}$ denotes a position of a j-th leaf of the MLC at a c-th control point, and $w_c$ denotes radiation energy of the treatment beam between the c-th control point and a (c+1)-th control point. The parameter $x_{cj}$ may be determined based on the target segment shape of the target segment parameters.

Optimal solutions for the target segment parameters may be determined by further optimizing the target segment parameters based on Equations (2) and (3) using a gradient descent algorithm. In this way, the optimization effect of the segment parameters may be improved, and the treatment effect of the VMAT treatment may enhanced.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A method implemented on a computing device having a processor and a computer-readable storage device, the method comprising:
   obtaining a plurality of beam angles of an arc for radiation treatment, wherein each of the plurality of beam angles is associated with at least one control point;
   obtaining preliminary segment parameters of control points associated with the plurality of beam angles, wherein preliminary segment parameters of each control point include a preliminary segment shape and a preliminary segment weight;
   determining target segment parameters of the control points by a target parameter determination process including:
      grouping the plurality of beam angles into at least two sets so that each pair of two consecutive beam angles of the plurality of beam angles belong to different sets of the at least two sets; and
      determining the target segment parameters of the control points in each of the at least two sets by optimizing, based on a leaf motion constraint, the preliminary segment parameters of the control points associating with the plurality of beam angles, wherein target segment parameters of each control point include a target segment shape and a target segment weight; and
   generating a treatment plan based on the target segment parameters of the control points in each of the at least two sets.

2. The method of claim 1, wherein the determining the target segment parameters of the control points in each of the at least two sets by optimizing, based on a leaf motion constraint, the preliminary segment parameters of the control points associating with the plurality of beam angles includes:
   determining the target segment parameters of the control points in each of the at least two sets by optimizing, based on a first leaf motion constraint and a second leaf motion constraint, the preliminary segment parameters of the control points associated with the plurality of beam angles, the first leaf motion constraint relating to a motion of a leaf of a collimator between a pair of consecutive beam angles among the plurality of beam angles, the second leaf motion constraint relating to a motion of a leaf of the collimator between a pair of consecutive control points of a beam angle.

3. The method of claim 2, wherein the second leaf motion constraint includes a target constraint, and the first leaf motion constraint is a specific multiple of the target constraint, the specific multiple being larger than or equal to 1.

4. The method of claim 2, wherein the determining the target segment parameters of the control points in each of the at least two sets by optimizing, based on a first leaf motion constraint and a second leaf motion constraint, the preliminary segment parameters of the control points associated with the plurality of beam angles includes:
   determining the target segment parameters of the control points in each of the at least two sets by simultaneously optimizing, based on the first leaf motion constraint and the second leaf motion constraint, the preliminary segment parameters of the control points in two or more of the at least two sets.

5. The method of claim 2, wherein the determining the target segment parameters of the control points in each of the at least two sets by optimizing, based on a first leaf motion constraint and a second leaf motion constraint, the preliminary segment parameters of the control points associated with the plurality of beam angles includes:
determining the target segment parameters of the control points in each of the at least two sets by optimizing, based on the first leaf motion constraint and the second leaf motion constraint, the preliminary segment parameters of the control points in the at least two sets in sequence, such that when preliminary segment parameters of control points in one of the at least two sets are being optimized, current segment parameters of control points in other sets of the at least two sets remain unchanged.

6. The method of claim 2, wherein the determining the target segment parameters of the control points in each of the at least two sets by optimizing, based on a first leaf motion constraint and a second leaf motion constraint, the preliminary segment parameters of the control points associated with the plurality of beam angles includes:
determining optimized segment parameters of the control points in each of the at least two sets by optimizing, based on the first leaf motion constraint and the second leaf motion constraint, the preliminary segment parameters of the control points in each of the at least two sets; and
determining the target segment parameters of the control points in each of the at least two sets in one or more iterations, each of the one or more iterations including:
decreasing the first leaf motion constraint by a decrement value;
updating the optimized segment parameters of the control points in each of the at least two sets based on the decreased first leaf motion constraint and the second leaf motion constraint;
determining whether a termination condition is satisfied; and
in response to determining that the termination condition is satisfied, designating updated segment parameters of the control points in each of the at least two sets as the target segment parameters of the control points in each of the at least two sets.

7. The method of claim 6, further including:
in response to determining that the termination condition is not satisfied, proceeding to a next iteration of the one or more iterations.

8. The method of claim 6, further including:
regrouping the plurality of beam angles into multiple sets such that each pair of two consecutive beams angles of the plurality of beam angles belong to different sets of the multiple sets; and
determining second optimized segment parameters of the control points in each of the multiple sets based on the decreased first leaf motion constraint, the second leaf motion constraint, and the updated segment parameters of the control points of the plurality of beam angles.

9. The method of claim 2, wherein the determining the target segment parameters of the control points in each of the at least two sets by optimizing, based on a first leaf motion constraint and a second leaf motion constraint, the preliminary segment parameters of the control points associated with the plurality of beam angles includes:
determining optimized segment parameters of the control points in each of the at least two sets by optimizing, based on the first leaf motion constraint and the second leaf motion constraint, the preliminary segment parameters of the control points in each of the at least two sets; and
decreasing the first leaf motion constraint by a decrement value;
determining whether a termination condition is satisfied; and
in response to determining that the termination condition is satisfied, designating the optimized segment parameters of the control points in each of the at least two sets as the target segment parameters of the control points in each of the at least two sets.

10. The method of claim 9, further including:
in response to determining that the termination condition is not satisfied,
updating the optimized segment parameters of the control points in each of the at least two sets based on the decreased first leaf motion constraint and the second leaf motion constraint; and
initiating one or more iterations, each of the one or more iterations including:
further decreasing the decreased first leaf motion constraint by the decrement value;
determining whether the termination condition is satisfied; and
in response to determining that the termination condition is satisfied, designating the updated segment parameters of the control points in each of the at least two sets as the target segment parameters of the control points in each of the at least two sets; and
in response to determining that the termination condition is not satisfied,
further updating the updated segment parameters of the control points in each of the at least two sets based on the further decreased first leaf motion constraint and the second leaf motion constraint; and
proceeding to a next iteration.

11. The method of claim 9, wherein the second leaf motion constraint includes a target constraint, the method further including:
determining whether the decreased first leaf motion constraint is smaller than the target constraint; and
in response to determining that the decreased first leaf motion constraint is smaller than the target constraint, adjusting the decreased first leaf motion constraint to the target constraint; and
determining third optimized segment parameters of control points in each of the at least two sets based on the adjusted first leaf motion constraint and the second leaf motion constraint; and
designating the third optimized segment parameters of the control points in each of the at least two sets as the target segment parameters of the control points in each of the at least two sets.

12. The method of claim 2, further including:
determining optimized segment parameters of the control points in each of the at least two sets by optimizing, based on the first leaf motion constraint and the second leaf motion constraint, the preliminary segment parameters of the control points in each of the at least two sets;
regrouping the plurality of beam angles into multiple sets such that each pair of two consecutive beams angles of the plurality of beam angles belong to different sets of the multiple sets; and determining second optimized segment parameters of the control points in each of the multiple sets based on the first leaf motion constraint, the second leaf motion constraint, and the optimized segment parameters of the control points of the plurality of beam angles.

13. The method of claim 1, wherein the preliminary segment parameters of the control points of the plurality of beam angles are determined based on a second leaf motion constraint.

14. A system, comprising:
at least one storage medium including a set of instructions; and
at least one processor configured to communicate with the at least one storage medium, wherein when executing the set of instructions, the at least one processor is configured to direct the system to perform operations including:
obtaining a plurality of beam angles of an arc for radiation treatment, wherein each of the plurality of beam angles is associated with at least one control point;
obtaining preliminary segment parameters of control points associated with the plurality of beam angles, wherein preliminary segment parameters of each control point include a preliminary segment shape and a preliminary segment weight;
determining target segment parameters of the control points by a target parameter determination process including:
grouping the plurality of beam angles into at least two sets so that each pair of two consecutive beam angles of the plurality of beam angles belong to different sets of the at least two sets; and
determining the target segment parameters of the control points in each of the at least two sets by optimizing, based on a leaf motion constraint, the preliminary segment parameters of the control points associating with the plurality of beam angles, wherein target segment parameters of each control point include a target segment shape and a target segment weight; and
generating a treatment plan based on the target segment parameters of the control points in each of the at least two sets.

15. The system of claim 14, wherein the determining the target segment parameters of the control points in each of the at least two sets by optimizing, based on a leaf motion constraint, the preliminary segment parameters of the control points associating with the plurality of beam angles includes:
determining the target segment parameters of the control points in each of the at least two sets by optimizing, based on a first leaf motion constraint and a second leaf motion constraint, the preliminary segment parameters of the control points associated with the plurality of beam angles, the first leaf motion constraint relating to a motion of a leaf of a collimator between a pair of consecutive beam angles among the plurality of beam angles, the second leaf motion constraint relating to a motion of a leaf of the collimator between a pair of consecutive control points of a beam angle.

16. The system of claim 15, wherein the second leaf motion constraint includes a target constraint, and the first leaf motion constraint is a specific multiple of the target constraint, the specific multiple being larger than or equal to 1.

17. The system of claim 15, wherein the determining the target segment parameters of the control points in each of the at least two sets by optimizing, based on a first leaf motion constraint and a second leaf motion constraint, the preliminary segment parameters of the control points associated with the plurality of beam angles includes:
determining the target segment parameters of the control points in each of the at least two sets by simultaneously optimizing, based on the first leaf motion constraint and the second leaf motion constraint, the preliminary segment parameters of the control points in two or more of the at least two sets.

18. The system of claim 15, wherein the determining the target segment parameters of the control points in each of the at least two sets by optimizing, based on a first leaf motion constraint and a second leaf motion constraint, the preliminary segment parameters of the control points associated with the plurality of beam angles includes:
determining the target segment parameters of the control points in each of the at least two sets by optimizing, based on the first leaf motion constraint and the second leaf motion constraint, the preliminary segment parameters of the control points in the at least two sets in sequence, such that when preliminary segment parameters of control points in one of the at least two sets are being optimized, current segment parameters of control points in other sets of the at least two sets remain unchanged.

19. The system of claim 15, wherein the determining the target segment parameters of the control points in each of the at least two sets by optimizing, based on a first leaf motion constraint and a second leaf motion constraint, the preliminary segment parameters of the control points associated with the plurality of beam angles includes:
determining optimized segment parameters of the control points in each of the at least two sets by optimizing, based on the first leaf motion constraint and the second leaf motion constraint, the preliminary segment parameters of the control points in each of the at least two sets; and
determining the target segment parameters of the control points in each of the at least two sets in one or more iterations, each of the one or more iterations including:
decreasing the first leaf motion constraint by a decrement value;
updating the optimized segment parameters of the control points in each of the at least two sets based on the decreased first leaf motion constraint and the second leaf motion constraint;
determining whether a termination condition is satisfied; and
in response to determining that the termination condition is satisfied, designating updated segment parameters of the control points in each of the at least two sets as the target segment parameters of the control points in each of the at least two sets.

20. A non-transitory readable medium, comprising at least one set of instructions, wherein when executed by at least one processor of a computing device, the at least one set of instructions directs the at least one processor to perform a method, the method comprising:
obtaining a plurality of beam angles of an arc for radiation treatment, wherein each of the plurality of beam angles is associated with at least one control point;
obtaining preliminary segment parameters of control points associated with the plurality of beam angles, wherein preliminary segment parameters of each control point include a preliminary segment shape and a preliminary segment weight;

determining target segment parameters of the control points by a target parameter determination process including:

grouping the plurality of beam angles into at least two sets so that each pair of two consecutive beam angles of the plurality of beam angles belong to different sets of the at least two sets; and determining the target segment parameters of the control points in each of the at least two sets by optimizing, based on a leaf motion constraint, the preliminary segment parameters of the control points associating with the plurality of beam angles, wherein target segment parameters of each control point include a target segment shape and a target segment weight; and generating a treatment plan based on the target segment parameters of the control points in each of the at least two sets.

* * * * *